United States Patent [19]

Biere et al.

[11] Patent Number: 4,772,610
[45] Date of Patent: Sep. 20, 1988

[54] 1-ALKYL ERGOLINYLTHIOUREA DERIVATIVES AND THEIR USE AS ANTIDEPRESSANT AGENTS

[75] Inventors: Helmut Biere; Gerhard Sauer; Helmut Wachtel, all of Berlin, Fed. Rep. of Germany

[73] Assignee: Schering Aktiengesellschaft, Berlin and Bergkamen, Fed. Rep. of Germany

[21] Appl. No.: 893,727

[22] Filed: Aug. 6, 1986

Related U.S. Application Data

[63] Continuation-in-part of Ser. No. 878,762, Jun. 26, 1986, which is a continuation of Ser. No. 452,521, Dec. 23, 1982, abandoned.

[30] Foreign Application Priority Data

Aug. 6, 1985 [DE] Fed. Rep. of Germany ....... 3528584

[51] Int. Cl.$^4$ ..................... A61K 31/48; C07D 457/12
[52] U.S. Cl. ........................................ 514/288; 546/68
[58] Field of Search ........................... 546/68; 514/288

[56] References Cited

U.S. PATENT DOCUMENTS

| | | | |
|---|---|---|---|
| 3,251,846 | 5/1966 | Semonsky et al. | 546/68 |
| 3,717,640 | 2/1973 | Arcari et al. | 546/67 |
| 4,500,712 | 2/1985 | Bernardi et al. | 546/67 |

FOREIGN PATENT DOCUMENTS

| | | | |
|---|---|---|---|
| 278853 | 2/1970 | Austria . | |
| 0082808 | 6/1983 | European Pat. Off. . | |
| 118848 | 9/1984 | European Pat. Off. | 546/68 |
| 1119843 | 12/1961 | Fed. Rep. of Germany . | |
| 2924102 | 12/1980 | Fed. Rep. of Germany | 546/68 |
| 3413657 | 10/1985 | Fed. Rep. of Germany | 546/68 |
| 3413659 | 10/1985 | Fed. Rep. of Germany | 546/68 |
| 2093452 | 9/1982 | United Kingdom | 546/67 |
| 3411981 | 10/1985 | United Kingdom | 546/68 |

OTHER PUBLICATIONS

Benes et al, CA 105-79217u (1986).
Votava et al, CA 67-31135k (1967).
Benes et al, CA 97-127876y (1982).
Haffer et al, CA 99-158703k (1983).
Cerny et al, CA 99-176130a (1983).

*Primary Examiner*—Donald G. Daus
*Assistant Examiner*—Cecilia Shen
*Attorney, Agent, or Firm*—Millen & White

[57] ABSTRACT

Novel 1-alkyl ergolinylthiourea derivatives of the general formula

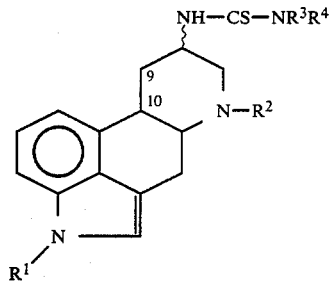

wherein
$R^1$ is $C_{1-6}$ alkyl,
$R^2$ and $R^3$ are $C_{1-4}$ alkyl,
$R^4$ is hydrogen or $C_{1-4}$ alkyl and
$C_9$—$C_{10}$ is a single bond or a double bond, and the acid addition salts thereof, with the provision that when $R^3$ and $R^4$ are both ethyl, $R^1$ and $R^2$ are not methyl and acid addition salts thereof are provided; as well as a process for the preparation of these compounds. The compounds are useful as medicinal agents, e.g., for the treatment of mental depression.

17 Claims, No Drawings

1-ALKYL ERGOLINYLTHIOUREA DERIVATIVES AND THEIR USE AS ANTIDEPRESSANT AGENTS

CROSS-REFERENCE TO RELATED APPLICATION

This application is related to Ser. No. 893,911 filed concurrently herewith which disclosure is incorporated by reference herein. This application is also a continuation-in-part of Ser. No. 878,762 filed June 26, 1986, which is a continuation of Ser. No. 452,521, filed Dec. 23, 1982. now abandoned.

BACKGROUND OF THE INVENTION

The invention relates to novel 1-alkyl ergolinylthiourea derivatives and to their preparation and their use as medicinal agents.

1-Methyl-ergolinylurea derivatives are described in U.S. Pat. No. 3,251,846. The 1-alkyl-ergolinylthiourea derivatives of this invention have an especially pronounced central $\alpha_2$-receptor blocking activity, in comparison with the ergoline urea derivatives.

OBJECTS OF THE INVENTION

It is an object of this invention to provide new such compounds having valuable pharmacological properties. It is another object to provide processes for the preparation and use of such compounds.

Upon further study of the specification and appended claims, further objects and advantages of this invention will become apparent to those skilled in the art.

SUMMARY OF THE INVENTION

In a composition aspect, these objects have been attained by providing 1-alkyl ergolinylthiourea derivatives of the general Formula I

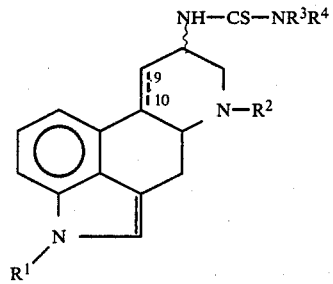

wherein
$R^1$ is $C_{1-6}$ alkyl or cycloalkyl,
$R^2$ and $R^3$ each is indepdnently $C_{1-4}$ alkyl,
$R^4$ is hydrogen or $C_{1-4}$ alkyl and
$C_9$—$C_{10}$ is a C—C single bond or a C—C double bond, and the acid addition salts thereof, with the provision that when $R^3$ and $R^4$ are both ethyl, $R^1$ and $R^2$ are not methyl.

In a method aspect, this invention relates to a process for the preparation of the compounds of the general Formula I, wherein the ergolinylurea derivative of general Formula II

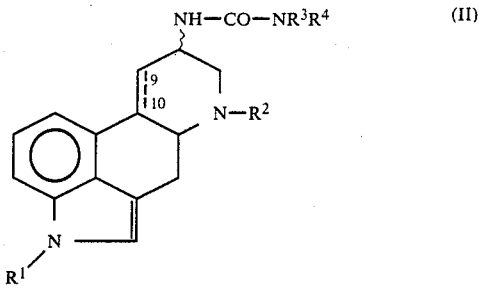

wherein $R^1$, $R^2$, $R^3$, $R^4$ and C===C have the meanings given above, is reacted with a chlorination agent and a thiolating agent.

DETAILED DISCUSSION $R^1$ contains up to 6 carbon atoms and is derived from aliphatic, straight-chain or branched and cyclic hydrocarbon residues, e.g., methyl, ethyl, n-propyl, isopropyl, cyclopropyl, n-butyl, tert-butyl, isobutyl, sec-butyl, cyclobutyl, n-pentyl cyclopentyl, hexyl, cyclohexyl, etc. The above-mentioned $C_1$-$C_4$ alkyls are preferred.

Examples of $R^2$, $R^3$, $R^4$ $C_{1-4}$ alkyl groups are methyl, ethyl, isopropyl, n-propyl, butyl, isobutyl and tert-butyl, sec-butyl, etc., $C_{1-2}$ alkyls are preferred for $R^3$ and $R^4$.

When $C_9$===$C_{10}$ is a single bond, the hydrogen atom in the 10-position is in the -position. The substituent in the 8-position can be in the $\alpha$- or $\beta$-position.

Pharmaceutically suitable salts of the compounds of this invention of Formula I are acid addition salts and are derived from customarily utilized acids, e.g., inorganic acids, e.g., hydrochloric acid, nitric acid, phosphoric acid, sulfuric acid, hydrobromic acid, hydriodic acid, nitrous acid or phosphorous acid, or they are derived from organic acids, e.g., aliphatic mono- or dicarboxylic acids, phenyl-substituted alkane-carboxylic acids, hydroxyalkane-carboxylic acids, or alkanedicarboxylic acids, aromatic acids or aliphatic or aromatic sulfonic acids, etc. Physiologically acceptable salts of these acids are, for example, the sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propiolate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthlate, terephthalate, benzenesulfonate, toluenesulfonate, chlorobenzenesulfonate, xylenesulfonate, phenylacetate, phenylpropionate, phenylbutyrate, citrate, lactate, $\beta$-hydroxybutyrate, glycolate, malate, tartrate, methanesulfonate, propanesulfonate, naphthalene-1-sulfonate, and naphthalene-2-sulfonate, etc.

The novel compounds of Formula I shown an especially pronounced central $\alpha_2$-receptor blocking activity, in comparison with the ergoline urea derivatives and ergoline thiourea derivatives which are not alkylated in the 1-position. Compounds having such a profile of effectiveness are particularly valuable for the treatment of psychic disturbances of depression related symptoms since, after central $\alpha_2$-receptor blockage, increased release of noradrenalin is effected in the brain, with the consequence of an anti-depressant therapeutic effect. Accordingly, the compounds of this invention are effective as anti-depressants. For example, they can be used to treat endogenous depression without identified specific causes. Typical symptoms which can be relieved include lack or loss of motivation, interest, concentration, hope or energy as well as feelings of emptiness. The compounds are also useful to treat excitability, subjective feelings of unrest, dysphoria and anxiety.

Central $\alpha_2$-receptor blockage of the compounds of this invention was demonstrated in an interaction test with the $\alpha_2$-receptor agonist clonidine on mice after a one-time i.p. pretreatment (parameter: relief of hypothermia caused by clonidine 0.1 mg/kg i.p.). Male NMRI mice were pretreated with various doses of comparison compounds and 1-alkylated 8-ergoline thioureas which do not, per se, affect the thermoregulation of the test animals. Other mice were pretreated with carrier medium. Thirty minutes later, all animals received clonidine 0.1 mg/kg i.p. Sixty minutes after the test compound and carrier medium (i.e., 30 minutes after clonidine), the rectal temperature was measured with the aid of a thermal probe. While the mice pretreated with carrier medium showed hypothermia, the effect of lowering body temperature, caused by clonidine, was cancelled out in correlation with the dose in animals pretreated with 1-substituted ergoline thioureas. Results for certain compounds are shown in the following table.

Compounds of Formula II are all conventionally available and are themselves prepared by fully conventional methods well known to those skilled in the art.

Processes of this invention have the advantages that chlorination of the indole does not occur and the double bonds do not react. Moreover, the process proceeds with complete retention of configuration.

In processes of this invention, the starting material of Formula II is treated with a chlorinating agent to convert it into a reactive ergoline salt. The salt is reacted with a thiolating reagent to produce the corresponding ergolin-8-ylthiourea derivative.

Suitable chlorinating agents including those like phosphorus oxychloride are preferred. Aggressive chlorinating agents like elemental chlorine are not suitable.

Preferably, the compound of Formula II is converted with phosphorus oxychloride into a reactive ergoline salt, and the latter is converted to the corresponding derivatives of Formula I with a thiolating reagent.

The conversion to the ergoline salt is performed in an inert, preferably aprotic solvent, for example in chlorinated hydrocarbons, such as dichloromethane, dichloroethane; ethers, such as diethyl ether, tetrahydrofuran, dioxane; ketones, such as acetone, methyl ethyl ketone; acetonitrile, etc.

The reaction temperature can vary widely, e.g., between about $-50°$ to $+80°$ C.; preferably from about $-20°$ C. to room temperature are preferred. Phosphorus oxychloride is preferably utilized in the reaction in a molar excess, preferably 2–10, more preferably 2–4 molar excess.

The thus-obtained activated ergoline urea salts can be isolated with exclusion of moisture or can be reacted with the thiolating agent without isolation.

Suitable thiolating agents are well known thio nucleophiles, such as, for example, alkali metal xanthates, alkali or alkaline earth sulfides, thiourea, Bunte salts, etc. Alkali metal xanthates, such as potassium ethylxanthate, potassium methylxanthate, and alkali metal sulfides, such as sodium sulfide, potassium sulfide, etc., are preferred.

All inert solvents are suitable for conducting the thiolating reaction, including the aforementioned ones as well as dimethylformamide, dimethylsulfoxide, etc., and also protic solvents, such as alcohols, e.g., ethanol, methanol, propanol, etc.

The reaction mixture can be maintained as a homogeneous mixture as well as a non-homogeneous mixture at low temperatures, e.g., from $-30°$ to $+20°$ C., yielding rapidly and completely the desired end products.

In general, the thiolation is effected at $-20°$ C. to room temperature, but in special cases it is also possible employ elevated temperatures, e.g., from $+20°$ to $+80°$ C., for acceleration and completion of the reaction.

The reaction goes to completion in 1–5 hours and is preferably performed under a protective gas atmosphere, such as, for example, under argon or nitrogen.

Alternatively, the compounds of Formula I can be prepared according to conventional methods.

For example, in process version (b) an amine of the general Formula III

TABLE

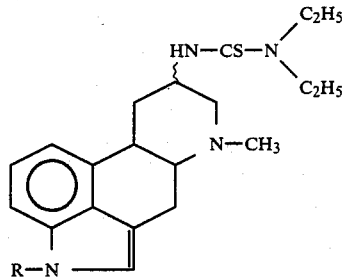

| R | No. of mice | Control | \multicolumn{8}{c}{Rectal Temperatures (°C.) Mean Value ± S.E.M. Dose of Test Substance (mg/kg)} |
|---|---|---|---|---|---|---|---|---|---|---|
| | | | 0.2 | 0.39 | 0.78 | 1.56 | 3.13 | 6.25 | 12.5 | 25 |
| H | 8 | 33.9 ± 0.3 | — | 33.9 ± 0.2 | 34.6 ± 0.3 | 35.0 ± 0.2 | 35.8 ± 0.2xx | 36.2 ± 0.3xx | — | — |
| CH$_3$ | 8 | 34.0 ± 0.2 | — | — | — | 34.6 ± 0.1 | 35.1 ± 0.1xx | 35.2 ± 0.2xx | 35.3 ± 0.2xx | — |
| C$_2$H$_5$ | 8 | 34.6 ± 0.3 | — | 34.8 ± 0.2 | 35.3 ± 0.3x | 35.7 ± 0.2xx | 35.7 ± 0.2xx | 35.8 ± 0.2xx | 36.6 ± 0.2xx | — |

(x = $p < 0.05$, xx = $p < 0.001$ vs Control/Variance Analysis/Dunnett-Test)

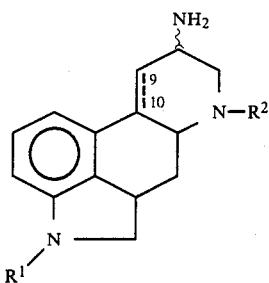

wherein $R^1$, $R^2$ and C___C are as defined above, is reacted with an isothiocyanate of the general formula $$R^3-N=C=S$$

wherein $R^3$ is as defined above;

or, in process version (c), an amine of general Formula III is reacted with 1,1'-thiocarbonyldiimidazole and an amine of the general formula $$NHR^3R^4$$

wherein $R^3$ and $R^4$ are as defined above.

All of the above process versions can be followed by converting the products thereof to the acid addition salts.

In the preparation of the compounds according to general Formula I by following process version (b), the reaction with the alkyl isothiocyanate takes place at room temperature or under slight heating, e.g., up to 70° C. in inert solvents, e.g., hydrocarbons, such as hexane, toluene, halogenated hydrocarbons, such as methylene chloride, ethers, such as diethyl ether, esters, such as ethyl acetate, etc., as well as the inert solvents mentioned above.

In the reaction with 1,1'-thiocarbonyldiimidazole according to process version (c), a reactive intermediate is formed which is reacted, without isolation, with a primary or secondary amine. The reaction is conducted in the inert solvents above at temperatures of from room temperature to, e.g., 70° C. and goes to completion in 1-3 hours.

For the formation of salts, the thus-obtained compounds of general Formula I are dissolved in a small amount of methanol or methylene chloride and combined with a concentrated solution of the desired acid in methanol at room temperature. Other solvents include ketones, such as acetone, methyl ethyl ketone, acetonitrile, etc.

The pharmacologically activecompounds of this invention can be processed in accordance with conventional methods of galenic pharmacy to produce products for administration to patients, e.g., mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinylpyrrolidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oil or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 0.05-2.0 mg. in a pharmaceutically acceptable carrier per unit dosage.

The dosage of the compounds according to this invention generally is 0.1-10 mg/day when administered to patients, e.g., humans as an antidepressant analogously to the known agent Idazoxan.

Dosages for a given host can be determined using conventional considerations, e.g., by customary comparison of the differential activities of the subject compound and of a known agent, e.g., by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

The preparation of the starting material is fully conventional according to methods well known to persons skilled in the art.

For example, the $N^1$-alkylation takes place as follows:

Preparation of
1,1-diethyl-3-(1,6-di-n-propyl-8α-ergolinyl)urea

Under nitrogen, 2 g of 1,1-diethyl-3-(6-n-propyl-8α-ergolinyl)urea, 2.7 g of pulverized KOH, 217 mg of tetrabutylammonium hydrogen sulfate, and 5.5 ml of n-propyl iodide are stirred in 100 ml of absolute tetrahydrofuran for 5 hours at room temperature. After addition of 50 ml of $H_2O$, the mixture is extracted with ethyl acetate, rinsed, and dried, yielding 1.8 g (80% of theory) as an oil.

$[\alpha]_D = +2.6°$ (c=0.5 $CHCl_3$)

EXAMPLE 1

1,1-Diethyl-3-(1-ethyl-9,10-didehydro-6-methyl-8α-ergolinyl)thiourea

A solution of 0.85 g of phosphorus oxychloride in 6 ml of dichloromethane is cooled to $-20°$ C. and then combined under nitrogen with 660 mg of 1,1-diethyl-3-(1-ethyl-9,10-didehydro-6-methyl-8α-ergolinyl)urea.

The reaction mixture is stirred for 5 hours at −20° C., then overnight at room temperature. After dichloromethane and excess POCl₃ have been removed by distillation, the residue is stirred together with absolute diethyl ether under exclusion of moisture, cooled, and the crystallized product is suctioned off. After the mixture has been made into a slurry in 5 ml of absolute acetonitrile, the mixture is cooled to −10° C., combined with 0.9 g of potassium ethylxanthate, and, under exclusion of moisture, stirred first for 2 hours at −10° C. and then another 4 hours at room temperature. Thereafter the acetonitrile is removed by distillation, the residue is combined with NaHCO₃ solution and ethyl acetate, the organic phase is separated, and the residue is chromatographed on silica gel. Yield: 480 mg (70% of theory); mp 108° C. (dichloromethane/pentane). $[\alpha]_D = +354°$ (c=0.5, CHCl₃)

EXAMPLE 2

1,1-Diethyl-3-(1,6-di-n-propyl-8-ergolinyl)thiourea

Obtained analogously to Example 1 from 1,1-diethyl-3-(1,6-di-n-propyl-8α-ergolinyl)urea. $[\alpha]_D = +39°$ (c=0.5, CHCl₃)

EXAMPLE 3

1,1-Diethyl-3-(1-ethyl-6-methyl-8α-ergolinyl)thiourea

A solution is prepared of 758 mg of 1,1-diethyl-3-(1-ethyl-6-methyl-8α-ergolinyl)urea in 75 ml of 1N hydrochloric acid and the solution is heated to 110° C. for 8 hours. Then the mixture is made alkaline with concentrated ammonium hydroxide solution and extracted by shaking with methylene chloride. The organic phase is dried with sodium sulfate and evaporated.

The crude product (8α-amino-1-ethyl-6-methylergoline) is dissolved in 30 ml of anhydrous methylene chloride, combined with 500 mg of N,N'-thiocarbonyldiimidazole, and stirred for one hour at room temperature. Then 1 ml of diethylamine is added thereto and the mixture is agitated for another hour at room temperature, 30 ml of water is added, the mixture is stirred for another 30 minutes, and then is worked up as described above. The residue is purified by chromatography on silica gel and crystallized.

Yield: 180 mg (17% of theory); $[\alpha]_D = +28°$ (c=0.5, chloroform).

The following compounds are prepared analogously:
1,1-Diethyl-3-(6-methyl-1-n-propyl-8α-ergolinyl)thiourea Yield: 14% (crystallized as tartrate) $[\alpha]_D = +37°$ (c=0.5, pyridine) 1,1-Diethyl-3-(6-methyl-1-isopropyl-8α-ergolinyl)thiourea.

Yield: 64%; $[\alpha]_D = +27°$ (c=0.5, chloroform).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1-Alkyl ergolinylthiourea of the formula

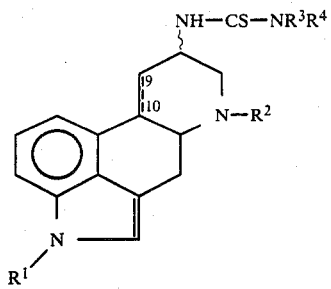

wherein
R¹ is C₁₋₆ alkyl or C₁₋₆ cycloalkyl,
R² and R³ each are C₁₋₄ alkyl,
R⁴ is hydrogen or C₁₋₄ alkyl and
C₉≡≡≡C₁₀ is a single or double bond, or a pharmaceutically acceptable acid addition salt thereof, with the provision that when R³ and R⁴ are both ethyl, R¹ and R² are not methyl.

2. A compound of claim 1, wherein C₉≡≡≡C₁₀ is a single bond.

3. A compound of claim 1, wherein C₉≡≡≡C₁₀ is a double bond.

4. A compound of claim 1, wherein R¹ is C₁₋₄ alkyl.

5. 1,1-Diethyl-3-(1-ethyl-9,10-didehydro-6-methyl-8α-ergolinyl)thiourea, a compound of claim 1.

6. 1,1-Diethyl-3-(1-ethyl-6-methyl-8α-ergolinyl)thiourea, a compound of claim 1.

7. 1,1-Diethyl-3-(1,6-di-n-propyl-8α-ergolinyl)thiourea, a compound of claim 1.

8. 1,1-Diethyl-3-(6-methyl-1-n-propyl-8α-ergolinyl)thiourea, a compound of claim 1.

9. 1,1-Diethyl-3-(6-methyl-1-isopropyl-8α-ergolinyl)thiourea, a compound of claim 1.

10. A pharmaceutical composition comprising an antidepressive-effective amount of a compound of claim 1 and a pharmaceutically acceptable carrier.

11. A pharmaceutical composition comprising an antidepressive-effective amount of a compound of claim 5 and a pharmaceutically acceptable carrier.

12. A pharmaceutical composition comprising an antidepressive-effective amount of a compound of claim 6 and a pharmaceutically acceptable carrier.

13. A pharmaceutical composition comprising an antidepressive-effective amount of a compound of claim 7 and a pharmaceutically acceptable carrier.

14. A pharmaceutical composition comprising an antidepressive-effective amount of a compound of claim 8 and a pharmaceutically acceptable carrier.

15. A pharmaceutical composition comprising an antidepressive-effective amount of a compound of claim 9 and a pharmaceutically acceptable carrier.

16. A method of treating depression in a patient in need of such treatment comprising administering thereto an antidepressant-effective amount of a compound of claim 1.

17. A method of blocking a central α₂-receptor comprising administering to a patient in need of such treatment an amount of a compound of claim 1 effective to back the central α₂-receptor.

* * * * *